United States Patent [19]
Heath et al.

[11] 3,972,902
[45] Aug. 3, 1976

[54] 4,4'-ISOPROPYLIDENE-BIS(3- AND 4-PHENYLENEOXYPHTHALIC ANHYDRIDE)

[75] Inventors: Darrell R. Heath; Joseph G. Wirth, both of Schenectady, N.Y.

[73] Assignee: General Electric Company, Schenectady, N.Y.

[22] Filed: Aug. 18, 1972

[21] Appl. No.: 281,749

Related U.S. Application Data

[63] Continuation-in-part of Ser. No. 108,151, Jan. 20, 1971, Pat. No. 3,787,475.

[52] U.S. Cl. .......................... 260/346.3; 260/2 EA; 260/78 TF; 260/465 F; 260/516; 260/517; 260/520 E
[51] Int. Cl.² ...................................... C07D 307/89
[58] Field of Search ................................ 260/346.3

[56] References Cited

FOREIGN PATENTS OR APPLICATIONS 2,030,905    11/1970    France
293,011      3/1971     U.S.S.R.

OTHER PUBLICATIONS

Wagner and Zook, Synthetic Organic Chemistry, New York, John Wiley pp. 412–415 and pp. 558–559.

Primary Examiner—Natalie Trousof
Assistant Examiner—Bernard Dentz
Attorney, Agent, or Firm—Joseph T. Cohen; Jerome C. Squillaro

[57] ABSTRACT

Aryloxy dianhydrides are prepared from the hydrolysis of the reaction product of a nitro-substituted phenyl dinitrile with a metal salt of a dihydroxy aryl compound in the presence of a dipolar aprotic solvent.

2 Claims, No Drawings

4,4'-ISOPROPYLIDENE-BIS(3- AND 4-PHENYLENEOXYPHTHALIC ANHYDRIDE)

This application is a continuation-in-part of application Ser. No. 108,151, filed Jan. 20, 1971, now U.S. Pat. No. 3,787,475.

This invention is concerned with a new class of aryloxy dianhydrides. Such compositions can be prepared by effecting reaction, in the presence of a dipolar aprotic solvent, of a mixture of ingredients comprising (1) a benzenoid compound of the general formula I 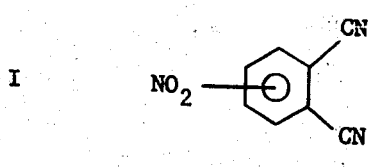

where the NO₂ group above can be positioned anywhere on the benzene ring, and (2) an alkali metal salt of an organic compound of the general formula Alk—O—R—O—Alk      II where R is a divalent aromatic radical, and Alk is an alkali metal atom.

The invention in particular is concerned with dianhydrides selected from the class consisting of (1) the compound 4,4'-isopropylidene-bis(3-phenyleneoxyphthalic anhydride, and (2) compounds of the general formula III 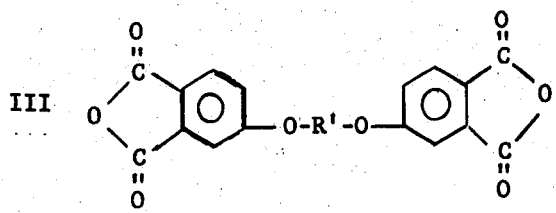

where R' is a member selected from the class consisting of (a) the following divalent organic radicals:

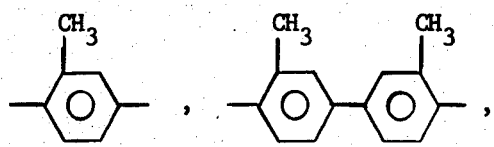

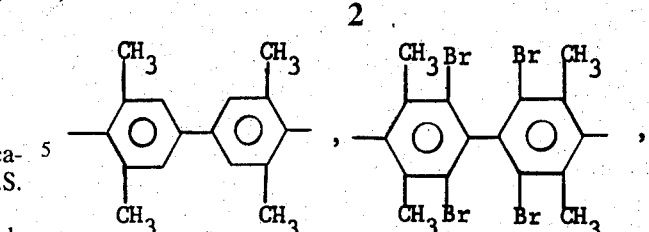

and 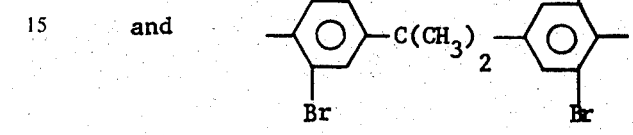

and (b) divalent organic radicals of the general formula

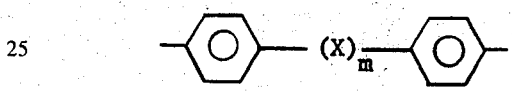

where X is a member selected from the class consisting of divalent radicals of the formulas

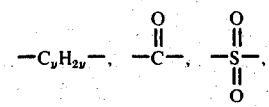

and —S—, where $m$ is 0 or 1, $y$ is a whole number from 1 to 5, and the divalent bonds of the —O—R'—O— radical are equally situated on the phthalic anhydride end groups, e.g., in the 3,3-positions or the 4,4-positions.

aryloxy derivatives of aromatic diacids have previously been prepared by different methods. The most common method consists in effecting a copper-catalyzed reaction between an alkali metal phenolate and a halo aromatic compound followed by oxidation of alkyl substituents to carboxylic acid groups. Thus, M. M. Koton and F. S. Florinski in Zh. Org. Khim., 4, 774 (1968) disclose the preparation of 4,4'-dioxyphenylene diphthalic acid by the copper catalyzed reaction of two equivalents of potassium-4,5-dimethylphenolate with 1,4-dibromobenzene for 4–5 hours at 220°–230° followed by potassium permanganate oxidation of the methyl groups to carboxylic acid groups. This method has two major limitations, the first being the known difficulty in reproducing copper-catalyzed reactions of alkali metal phenolates with halo aromatic compounds and the high temperatures required to effect these reactions, and the second being that any group susceptible to oxidation will be oxidized along with the groups which are desired to be oxidized.

We have without success attempted to effect direct reaction between a nitro derivative of an aromatic diacid and an alkali metal phenolate in a dipolar aprotic solvent. For example, the reaction of sodium phenoxide and 4-nitrophthalic acid failed to give any product corresponding to the formula

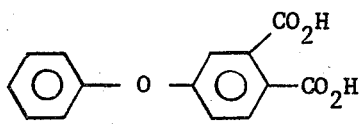

Unexpectedly, we have discovered that although the reaction between sodium phenolate and the nitro acid will not take place with 3-nitrophthalic acid, we are able to make aryloxy derivatives of these acids if reaction is effected between a metal phenolate, with phthalic acid when the acid is in the form of the corresponding nitrophthalonitrile. This reaction between the metal phenolate and the nitrile usually results in high yields of the phenoxy derivative. The phthalic derivative can then be obtained by hydrolysis of the cyano group. In the case of the aryloxy phthalic acids, various well known procedures can be used for conversion to the anhydride form.

By virtue of our invention, we are able to prepare numerous tetrabasic acids by reaction of a compound of formula I with a metal salt of formula II. In effecting the above reactions, it is important that one use a dipolar aprotic solvent in the reaction of the cyano derivatives of the compounds of formula I. The particular advantages of our invention over the prior art are the mild conditions under which reactions can be carried out; often room temperature is sufficient to effect reaction, generally high yields of products are obtained, the commercially attractive potential of synthesizing aromatic acids containing oxidizable groups (which is impractical to accomplish by presently known prior art methods), and the ability to produce diacids and dianhydrides of a broad scope.

Among the divalent alkyl radicals which the grouping $-C_yH_{2y}$ may represent are, for instance, methylene, ethylene, trimethylene, isopropylidene ($-C(CH_3)_2-$), butylene, amylene, etc. Typical of dihydroxy diarylene compounds from which the metal salt of formula II may be prepared by reacting the aforesaid diarylene compound with two mols of an alkali-metal hydroxide may be mentioned:

2,2-bis-(2-hydroxyphenyl)propane;
2,4'-dihydroxydiphenylmethane;
bis-(2-hydroxyphenyl)-methane;
2,2-bis-(4-hydroxyphenyl)-propane hereinafter identified as "bisphenol-A" or "BPA";
1,1-bis-(4-hydroxyphenyl)-ethane;
1,1-bis-(4-hydroxyphenyl)-propane;
2,2-bis-(4-hydroxyphenyl)-pentane;
3,3-bis-(4-hydroxyphenyl)-pentane;
4,4'-dihydroxybiphenyl
4,4'-dihydroxy-3,3',5,5'-tetramethylbiphenyl
2,4dihydroxybenzophenone;
4,4'-dihydroxydiphenyl sulfone;
2,4'-dihydroxydiphenyl sulfone;
4,4'-dihydroxydiphenyl sulfoxide;
4,4'-dihydroxydiphenyl sulfide; etc.

The means whereby the present invention may be practiced can be varied widely. When dialkali metal salts of formula II are used with the benzenoid compounds of formula I, the molar ratio is advantageously at least 2 mols of the compound of formula I per mol of the metal salt of formula II. Excess molar quantities of the compound of formula I over the molar quantity of the metal salt of formula II may be employed without departing from the scope of the invention; thus from 2 to 4 or more mols of the compound of formula I may be used per mol of the metal salt of formula II.

In making the metal salts of formula II, it is sometimes advantageous to preform these salts by reacting the corresponding dihydroxy organic compound with an alkali-metal hydroxide such as sodium hydroxide, potassium hydroxide, etc. For instance, the dialkali metal salt of bisphenol-A may be obtained by reacting 2 mols of sodium hydroxide per mol of bisphenol-A. Persons skilled in the art will have no difficulty in determining how to make the alkali-metal salts of formula II for use with the compounds of formula I.

Alternatively, the dihydroxy diarylene compound, e.g., the bisphenol, may be converted to its alkali metal salt during reaction with the compounds of formula I by addition of an alkali metal carbonate in adequate molar concentrations to a reaction mixture composed of the compound of formula I and the precursor hydroxy aromatic compound required to form the metal salts of formula II.

The conditions of reaction whereby the metal salts of formula II are reacted with the compounds of formula I can be varied widely. Generally, temperatures of the order of about 20° – 150° C. are advantageously employed, although it is possible to employ lower or higher temperature conditions depending on the ingredients used, the reaction product sought, time of reaction, solvent employed, etc. In addition to atmospheric pressure, superpressures and sub-atmospheric pressures may be employed, depending upon the other conditions of reaction, the ingredients used, the speed at which it is desired to effect reaction, etc.

The time of reaction also can be varied widely depending on the ingredients used, the temperature, the desired yield, etc. It has been found that times varying from a few minutes to as much as 60 to 80 hours or more are advantageously employed to obtain the maximum yield. Thereafter the reaction product can be treated in the manner required to effect precipitation and/or separation of the desired reaction product. Generally, common solvents such as diethyl ether, water, etc., are employed for the purpose. For purification purposes, the final product can be redistilled or recrystallized in manners well known in the art.

It is important that the reaction between the compounds of formula I and the metal salts of formula II be carried out in the presence of a dipolar aprotic solvent. The term "dipolar aprotic solvent" is intended to mean any organic solvent which has no active protons which may interfere with the reaction herein described. As will be evident to those skilled in the art, any dipolar aprotic solvent which is capable of dissolving the reactants and causing intimate contact of the reaction ingredients may be used.

Among the preferred aprotic solvents which may be employed in the practice of this invention are non-acid, oxygen-containing, nitrogen-containing organic solvents. These include but are not limited to, for instance, N,N-dimethylacetamide, N-methylpyrrolidone, N,N-dimethylformamide, dimethylsulfoxide (DMSO), etc.

The amount of solvent used in the reaction mixture may be varied widely. Generally, on a weight basis, one can employ from 0.5 to 50 or more parts of the solvent per part of total weight of the reactants, namely, the compounds of formula I and the metal compounds of formula II. The amount of solvent is not critical, but generally we have found that on a weight basis one can employ from 2 to 20 parts of the solvent per part of the total weight of the compounds of formula I and the metal compounds of formula II.

Once the tetranitrile of the general formula

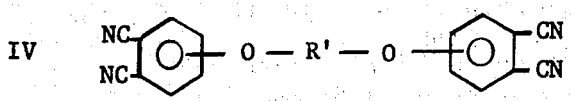

where R' has the meanings given above is formed, it is relatively easy, using techniques well-known in the art, to convert the tetranitrile to the corresponding tetracarboxylic acid and thereafter dehydrate the tetracarboxylic acid to the corresponding desired dianhydride. For example, the tetranitrile can be treated with potassium hydroxide in a mixture of aqueous methanol and then heated at reflux for a period of time to give the tetra acid. Acidification of the tetra-acid reaction mixture with, for instance, hydrochloric acid, permits the tetra-acid to separate. Thereafter, heating at elevated temperatures, for example, at about 200° to 300° C. will effect dehydration of the tetra-acid to the corresponding dianhydride.

In order that those skilled in the art may better understand how the present invention may be practiced, the following examples are given by way of illustration and not by way of limitation. Unless otherwise stated, all parts are by weight.

EXAMPLE 1

Bis(3,4-dicyanophenyl)ether of bisphenol-A was prepared as follows. A mixture of 1.71 grams (0.0075 mol) bisphenol-A, 0.6 gram (1.1881 grams 50.5% aqueous solution, 0.015 mol) sodium hydroxide, 20 ml. nitrogen-sparged DMSO, and 15 ml. benzene was stirred at reflux under nitrogen over a Dean-Stark trap for 4 hours and the benzene was then removed by distillation. The reaction mixture was cooled to room temperature and 2.595 grams (0.015 mol) 4-nitrophthalonitrile was added. The mixture was stirred under nitrogen at room temperature for 1.5 hours and was then poured into 100 ml. of water. The product which separated from the aqueous solution as a white powder was extracted into methylene chloride and the extract was washed with water, dried with sodium sulfate, and filtered. The solvent was removed and the residue was recrystallized from toluene/hexane solution to give 3.1 grams (86% yield) of a white grannular solid, melting point 195°–196° C. This product was identified as the above compound by infra red and by elemental analyses.

|  | Found | Calculated |
|---|---|---|
| %C | 77.6 | 77.5 |
| %H | 4.24 | 4.17 |
| %N | 11.8 | 11.66 |

This compound had the formula

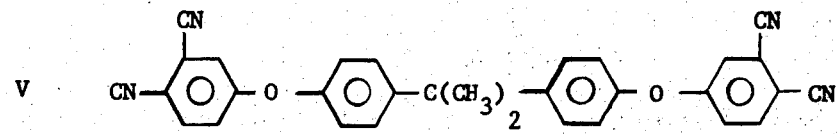

EXAMPLE 1A

A mixture of 1.2 grams (0.0025 mol) of the bis(3,4-dicyanophenyl) ether of bisphenol-A described in Example 1, 5.61 grams (0.1 mol) potassium hydroxide, and 20 ml. of aqueous methanol was stirred at reflux temperature of the mass for seven days after which the mixture was acidified with hydrochloric acid and the oily liquid which separated solidified on standing. The solid material was filtered and dried in vacuum. Thereafter, the reaction product was dehydrated by heating it at 250° C. and then distilled at 350° C. (0.1 mm.) to give 2,2-bis-[4-(3,4-dicarboxyphenoxy)phenyl]propane dianhydride in about a 92% yield. The product which melted at 187°–189° C. was identified as having the formula

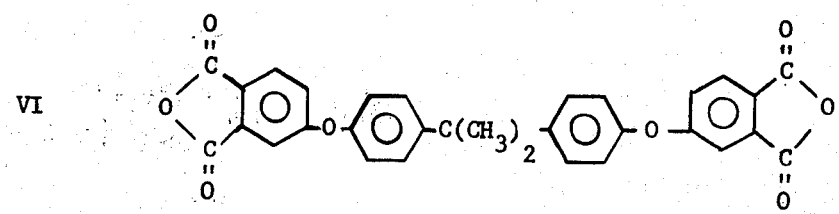

as evidenced by the following analyses:

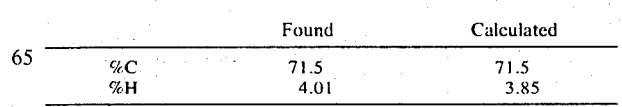

|  | Found | Calculated |
|---|---|---|
| %C | 71.5 | 71.5 |
| %H | 4.01 | 3.85 |

EXAMPLE 2

1,4-Bis(3,4-dicyanophenoxy)benzene was prepared by first forming a mixture of 1.10 grams (0.01 mol) hydroquinone, 3.56 grams (0.02 mol) 4-nitrophthalonitrile, 2.76 grams (0.02 mol) anhydrous potassium carbonate, and 15 ml. of dry, nitrogen-sparged DMSO. This was stirred under nitrogen at room temperature for 24 hours and the mixture was poured into 200 ml. of water. The precipitate was filtered, washed with water, dried "in vacuo" and dissolved in 250 ml. boiling acetonitrile. The product crystallized from the acetonitrile as fine pale blue needles amounting to 2.2 grams (61% yield). The crystallized product was distilled at 300°–310° C. (0.05 mm) to yield an oil which solidified on cooling. This solid material was recrystallized from acetonitrile to give 2.1 grams of the desired compound, melting point 255°–257° C. whose identity was established by infra red and by elemental analyses.

|     | Found | Calculated |
| --- | --- | --- |
| %C  | 72.7  | 72.9 |
| %H  | 2.70  | 2.75 |
| %N  | 15.6  | 15.45 |

EXAMPLE 3

A mixture of 0.93 gram (0.005 mol) 4,4'-dihydroxybiphenyl, 0.4 gram (0.792 gram of 50.5% aqueous solution, 0.01 mol) sodium hydroxide, 20 ml. nitrogen-sparged DMSO, and 20 ml. benzene was stirred under a nitrogen atmosphere at reflux temperature over a Dean Stark trap for 18 hours and the benzene was then removed by distillation. The mixture was cooled to room temperature, 1.73 grams (0.01 mol) 4-nitrophthalonitrile was added, and stirring under nitrogen at 25° C. was continued for 40 hours. The mixture was poured into 200 ml. of water and the product, a white granular solid, was filtered and washed with water. Recrystallization from acetonitrile gave 2.10 grams of product (96.0% yield), melting point 233-233.5° C. The identity of the product as 4,4'-bis-(3,4-dicyanophenoxy)biphenyl was established by infra red and by elemental analyses.

|     | Found | Calculated |
| --- | --- | --- |
| %C  | 76.4  | 76.74 |
| %H  | 3.1   | 3.20 |
| %N  | 12.7  | 12.38 |

EXAMPLE 2A

A mixture of 0.905 gram (0.0025 mol) of the 1,4-bis(3,4-dicyanophenoxy) benzene of Example 2, 5.6 grams (0.1 mol) of potassium hydroxide, and 20 ml. of aqueous methanol was stirred at the reflux temperature of the mass for about one week. The mixture was acidified with hydrochloric acid, and the tetra-acid derivative separated from the cold aqueous solution as fine, silvery needles. The latter tetra-acid was dehydrated by heating at 275° C. and was then distilled at 300° C. (0.1 mm.) to give the hydroquinone-bis(4-phthalic anhydride) diether in about a 99% yield. This dianhydride which had a melting point of 264°–266° C. had the formula VII 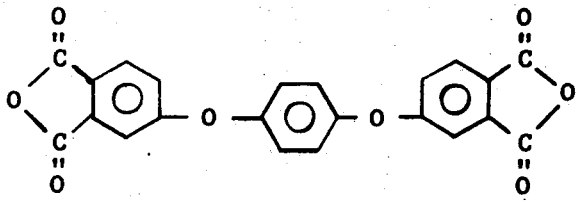

as evidenced by the following analyses:

|     | Found | Calculated |
| --- | --- | --- |
| %C  | 65.6  | 65.7 |
| %H  | 2.6   | 2.48 |

EXAMPLE 3A

A mixture of 1.095 grams (0.0025 mol) of 4,4'-bis-(3,4-dicyanophenoxy)biphenyl of Example 3, 5.61 grams (0.1 mol) potassium hydroxide, and 20 ml. of aqueous methanol was stirred at the reflux temperature of the mass for about one week. The mixture was acidified with hydrochloric acid and the tetra-acid which precipitated was isolated by filtration, washed with water and dried in vacuum. This tetra-acid was dehydrated by heating it at 275° C., and was then distilled at 350° C. (0.1 mm.) to give 4,4'-bis(phenyleneoxyphthalic anhydride) melting at 286°–288° C. This composition which had the formula VIII 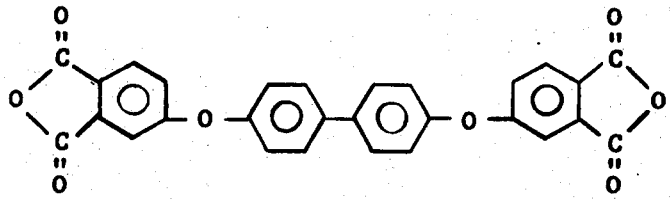

was identified by the following elemental analyses:

|     | Found | Calculated |
| --- | --- | --- |
| %C  | 70.2  | 70.3 |
| %H  | 3.08  | 2.93 |

EXAMPLE 4

A mixture of 1.25 grams (0.005 mol) 4,4'-dihydroxydiphenyl sulfone, 0.4 gram (0.791 gram 50.5% aqueous solution, 0.01 mol) sodium hydroxide, 20 ml. nitrogen-sparged DMSO, and 20 ml. of benzene was stirred under nitrogen atmosphere at reflux over a Dean Stark trap for 18 hours and the benzene was removed by distillation. The mixture was cooled to room temperature and 1.73 grams (0.01 mol) of 4-nitrophthalonitrile was added and stirring was continued at room temperature (about 26°–28° C.) in air for 40 hours. The homogeneous solution thus obtained was poured into 200 ml. of water and the precipitate which separated was isolated by filtration, washed with water, dried "in vacuo" and recrystallized from acetonitrile. The product separated from the cooled solution as golden needles and was filtered and dried "in vacuo" to give 1.5 grams (60%) yield, melting point 229°–230° C. of 4,4'-bis-(3,4-dicyanophenoxy)diphenylsulfone. The product was identified as such by infra red and by elemental analyses.

|     | Found | Calculated |
| --- | ----- | ---------- |
| %C  | 66.6  | 66.93      |
| %H  | 2.8   | 2.79       |
| %N  | 11.3  | 11.14      |
| %S  | 6.3   | 6.38       |

EXAMPLE 5

To a mixture of 1.73 grams (0.010 mol) 4-nitrophthalonitrile, 1.00 gram (0.005 mol) 4,4'-methylenediphenol and 1.38 grams anhydrous potassium carbonate was added 10 ml. nitrogen-sparged DMSO. The resulting mixture was stirred for about 18 hours at room temperature and the poured into water. The white precipitate which formed was collected and recrystallized from ethanol-water to give 2.0 grams (80% yield) 4,4'-bis(3,4-dicyanophenoxy)-diphenylmethane. The identity of this compound was identified by infra red and by elemental analysis.

|     | Found | Calculated |
| --- | ----- | ---------- |
| %C  | 77.1  | 77.4       |
| %H  | 3.5   | 3.13       |
| %N  | 12.3  | 12.4       |

EXAMPLE 5A

The 4,4'-bis(3,4-dicyanophenoxy)diphenyl methane described in Example 5, can be treated with potassium hydroxide in aqueous methanol, acidified with hydrochloric acid to yield the tetra-acid derivative, and the tetra-acid derivative can be dehydrated in the same manner as described in Examples 1A, 2A, and 3A to yield the dianhydride of the formula

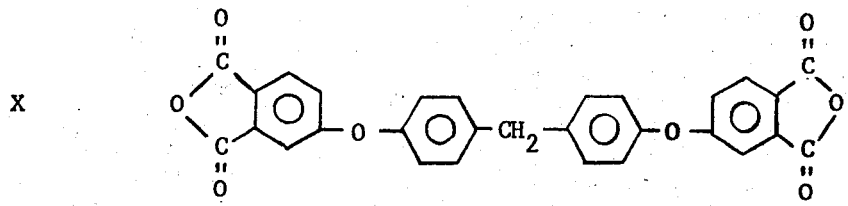

X

EXAMPLE 4A

When the 4,4'-bis-(3,4-dicyanophenoxy)diphenyl sulfone of Example 4 is reacted with potassium hydroxide and aqueous methanol and thereafter acidified with hydrochloric acid, and thereafter the formed tetra-acid is separated and dehydrated in the same manner as in Examples 1A, 2A, and 3A, there is obtained the corresponding dianhydride of the general formula

EXAMPLE 6

A mixture of 1.24 grams (0.01 mol) of 2-methyl hydroquinone, 3.46 grams (0.02 mol) 4-nitrophthalonitrile, 3.45 grams (0.025 mol) potassium carbonate, and 25 cc of dimethyl sulfoxide was stirred under a nitrogen atmosphere at about 25° to 30° C. for about 16 hours. The solution was diluted with 300 cc water and the solid material which separated was filtered and dried in vacuum to give 3.4 grams (about a 90% yield) of a product which when recrystallized from methyl isobutyl ketone yielded white granules melting at 207°–208° C. and identified as the tetranitrile having the formula

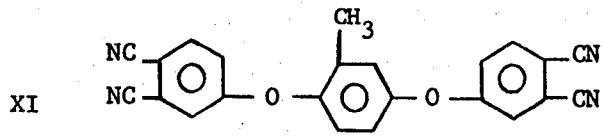

XI

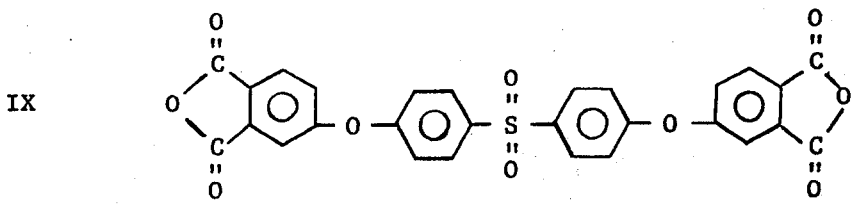

IX

A mixture of 0.94 gram (0.0025 mol) of this nitrile, 5.61 grams (0.1 mol) potassium hydroxide and 20 cc of aqueous methanol was stirred at the reflux temperature for about 72 hours. The mixture was then acidified with hydrochloric acid and a white precipitate which deposited was filtered and dried in vacuum at about 100° C. The tetra-acid product so obtained was dehydrated by heating to 275° C. and then distilling at 300° C. to give a colorless oil, which upon cooling gave a white solid melting at about 214°–216° C. This material was identified as having the formula

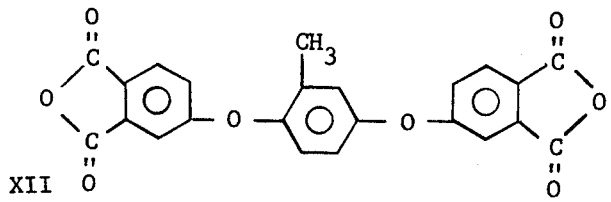

by the following analyses:

|  | Found | Calculated |
|---|---|---|
| %C | 66.6 | 66.3 |
| %H | 3.10 | 2.88 |

EXAMPLE 7

A mixture of 2.12 grams (0.01 mol) 4,4'-dihydroxy-3,3'-dimethyl biphenyl, 3.46 grams (0.02 mol) 4-nitrophthalonitrile, 3.45 grams (0.025 mol) potassium carbonate, and 25 cc of dimethyl sulfoxide was stirred under a nitrogen atmosphere at about 25° to 30° C. for approximately 16 hours. The mixture was added to 300 cc of water and the resulting precipitate was filtered, and dried in vacuum to give 4.5 grams (about a 97% yield) of a tetranitrile which when recrystallized from methyl isobutyl ketone yielded yellow granules melting at 238°–241° C. and having the formula

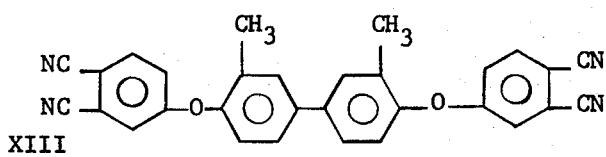

About 1.35 grams (0.0029 mol) of this tetranitrile, 5.6 grams (0.1 mol) potassium hydroxide, and 20 cc aqueous methanol was stirred at reflux for about 72 hours, the solution acidified with hydrochloric acid and the precipitate which was obtained was filtered and dried in vacuum at about 100° C. The resulting tetra-acid was dehydrated at 250° C. and then distilled at 350° C. (0.1 mm) to give a product which upon cooling yielded a yellow solid melting at 246°–249° C. This was identified as the dianhydride corresponding to the formula

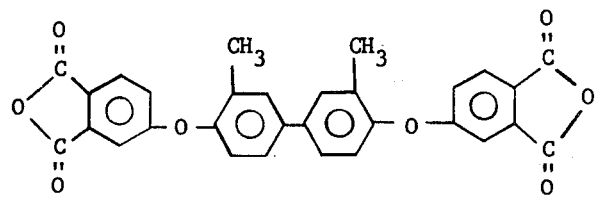

whose identity was established by the following analyses:

|  | Found | Calculated |
|---|---|---|
| %C | 71.2 | 71.1 |
| %H | 3.8 | 3.56 |

EXAMPLE 8

A mixture of 2.283 grams (0.01 mol) of bisphenol-A, 0.8 gram (1.6 grams of a 50% aqueous solution, 0.02 mol) sodium hydroxide, 25 cc dimethyl sulfoxide, and 15 cc toluene was stirred in a nitrogen atmosphere at reflux temperature over a Dean-Stark trap for about 15 hours. The residual mixture was then cooled to 25° C. and 3.46 grams (0.02 mol) of 3-nitrophthalonitrile and 10 cc of dimethyl sulfoxide were added. After stirring for about 3 hours at 25° C., the mixture was added to 350 cc water and the resulting precipitate was filtered, washed with water and dried in vacuum at 70° C. to give 4.8 grams (about 100% yield) of a product which when recrystallized from ethyl acetate gave silvery needles having two sharp melting points: 161°–163° C., and 179°–180° C. (indicating polymorphism) for the tetranitrile derivative having the formula

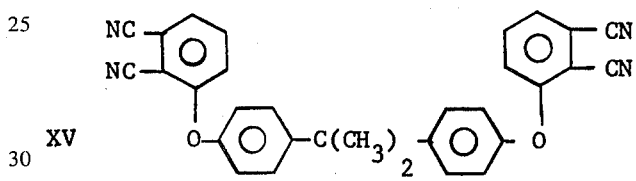

About 1.39 grams (0.0029 mol) of this bisphenol-A nitrile, 5.6 grams (0.1 mol) potassium hydroxide, and 20 cc of aqueous methanol was stirred at the reflux temperature of the mass for about 72 hours. The mixture was acidified with hydrochloric acid and the formed precipitate was filtered and dried in vacuum. The reaction product was then stirred at reflux temperature with 7 cc of glacial acetic acid and 0.5 cc acetic anhydride. After cooling, the solids were filtered, and then dissolved in a boiling toluene/acetic acid mixture, filtered hot and cooled. The product which precipitated in the form of white granules melted at 186°–188° C., and was identified as 2,2-bis-[4-(2,3-dicarboxyphenoxy)phenyl]propane dianhydride and having the formula

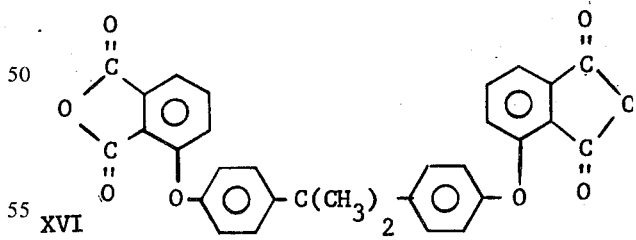

by the following analyses:

|  | Found | Calculated |
|---|---|---|
| %C | 72.3 | 71.5 |
| %H | 4.5 | 3.85 |

EXAMPLE 9

Employing the same conditions as were used in the preceding examples, the tetranitriles prepared from the reaction of 4-nitrophthalonitrile and either 4,4'-dihydroxy-3,3',5,5'-tetramethylbiphenyl and 4,4'-dihydroxy benzophenone can be hydrolyzed and dehydrated to give the respective dianhydrides having the formulas XVII 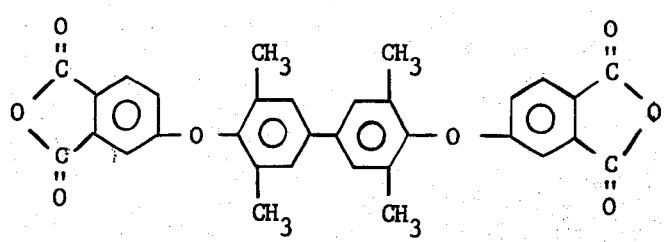

and

XVIII 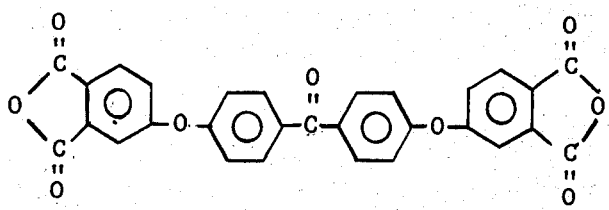

EXAMPLE 11

The tetranitrile derived from the reaction of 4-nitrophthalonitrile and 4,4'-dihydroxydiphenyl sulfide, can be hydrolyzed to the corresponding tetra-acid and thereafter dehydrated to the dianhydride employing the procedures described in the foregoing examples to give the dianhydride compound having the formula XIX 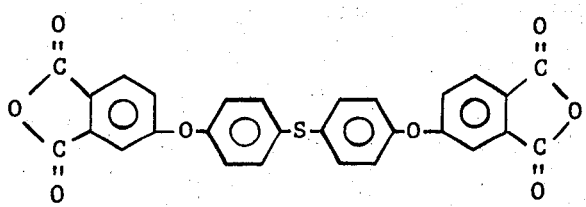

EXAMPLE 12

The tetracyano derivative of tetrabromotetramethylbiphenol can be prepared similarly as in the foregoing examples by effecting reaction between tetrabromotetramethylbiphenol and 4-nitrophthalonitrile to give the compound having the formula XX 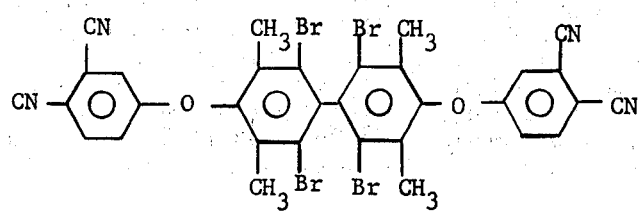

When the aforesaid tetracyano derivative is hydrolyzed to the tetra-acid derivative and then dehydrated using the procedures described in the preceding examples, one obtains the dianhydride having the formula XXI 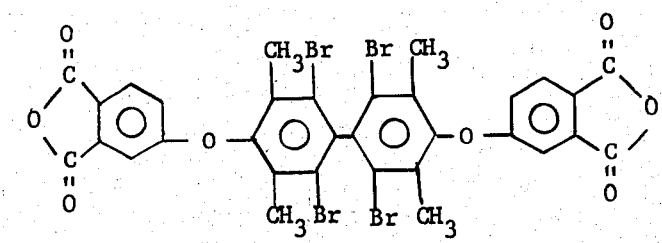

EXAMPLE 13

The tetracyano derivative of the reaction product of tetrabromo-bisphenol-A and 4-nitrophthalonitrile was prepared by stirring at room temperature under nitrogen for 18 hours a mixture of 3.46 grams (0.02 mol) 4-nitrophthalonitrile, 5.44 grams (0.01 mol) of the 2,2',6,6'-tetrabromo derivative of BPA, 6.9 grams (0.05 mol) potassium carbonate and 30 ml. DMSO. The mixture was then heated at about 55° C. for a total of 50 hours, thereafter diluted with 600 ml. 1N HCl, filtered, the solid material air-dried and then dissolved in 500 ml. benzene. After treatment with carbon for decolorizing purposes and filtering, the solution was then concentrated to 400 ml., 200 ml. cyclohexane was added and the mixture concentrated to 300 ml. for recrystallization purposes. The product which settled out was dried for about 18 hours and on analysis was found to be the desired tetracyano derivative having the formula (m.p. 251°–255° C.)

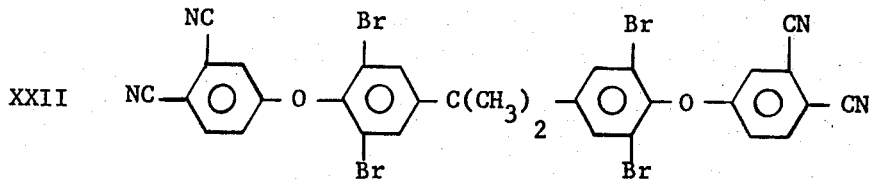

The analyses were follows:

|  | Found | Calculated |
|---|---|---|
| %C | 47.2 | 46.8 |
| %H | 2.3 | 2.0 |
| %N | 7.0 | 7.0 |

When this tetracyano derivative is hydrolyzed and then dehydrated similarly as in the previous examples, one obtains the dianhydride having the formula

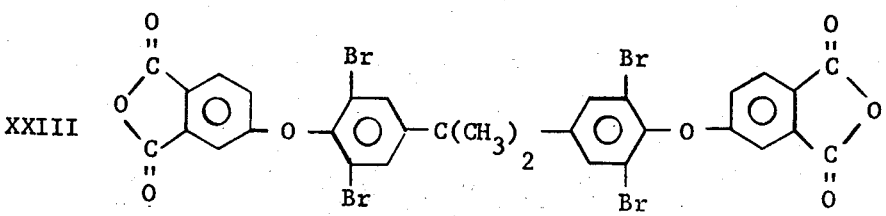

The dianhydride compositions herein described have many uses. One of the more important uses to which these compositions may be put are as intermediates in the preparation of heat-resistant polyimides which have many known uses. For instance, these dianhydrides may be reacted with various aromatic diamines such as 4,4'-diaminodiphenyl oxide, 4,4'-diaminodiphenyl methane, 4,4'-diaminodiphenyl sulfone, etc., to give aromatic polyamide acids of the type more particularly described in U.S. Pat. No. 3,179,614, issued Apr. 20, 1965. These polyamide acids can then be heated to cyclize the amide acid portions to give polyimide resins of the type described in U.S. Pat. No. 3,179,634, issued on the same date as the preceding patent.

As a specific example, a polyimide preparation utilizing the dianhydride described in Example 1A could be reacted, for instance, with 4,4'-diaminodiphenyloxide to give the polyamide acid which upon heating at elevated temperatures of about 150° to 250° C., is cyclized to give the corresponding aromatic polyimide.

The polymeric composition derived from the reaction of dianhydrides herein described have many applications. These polymeric compositions may be used to form fibers, films, or molded products. Thus, either by extrusion from melt or by depositing from solution, fibers derived from these polymeric compositions may be formed and used in the preparation of various textile materials designed for clothing and similar applications. In addition, solutions of the polymers can be used to coat electrical conductors for insulation purposes.

The dianhydrides herein described and claimed also have utility as curing agents for epoxy resins. When used for this purpose, they are capable of accelerating the cure of such resins to form useful products in the molded and electrical arts.

Various fillers may be incorporated in the polymeric compositions prior to molding thereof. Among such fillers may be mentioned glass fibers, carbon black, titanium dioxide, silica, mica, bentonite, etc. Molded products derived from such a mixture of ingredients can be used as gears, handles for cooking utensils, etc. The incorporaton of abrasive particles such as carborundum, diamond powder, etc., makes molded products derived from such polymeric compositions useful as grinding wheels, etc. The addition of carbon, silicon carbide, powdered metal, conducting oxides, etc., to the polymeric compositions results in the so-called resistance of semiconducting paints which have many useful applications.

The above-mentioned polymeric compositions can also be incorporated into other materials to modify the properties of the latter. For example, they may be compounded with substances such as natural or synthetic rubbers, natural resins such as rosin, copal, shellac, etc.; synthetic resins such as phenol-aldehyde resins, alkyd resins, vinyl resins, esters of acrylic and methacrylic acid, etc.; cellulosic materials such as paper, inorganic and organic esters of cellulose such as cellulose nitrate, cellulose acetate, cellulose ethers, such as methyl cellulose, ethyl cellulose, etc.

Laminated products may be made by superimposing organic or inorganic fiber sheet materials coated and impregnated with the polymeric compositions and thereafter bonding the sheets under heat and pressure. Shaped articles formed from such compositions under heat and pressure in accordance with the practices now widely used in the plastics art have a number of well-known applications such as in the decorative field, electrical board field, etc.

It will of course be apparent to those skilled in the art that other conditions of reaction in addition to those specifically described in the foregoing examples may be employed without departing from the scope of the invention. Thus, it is apparent that many of the conditions outlined previously can be used for making the compositions herein described and claimed. Also, it will be apparent that the ingredients chosen for making the desired reaction products can be varied widely, many examples of which have been given above.

What we claim as new and desire to secure by Letters Patent of the United States:

1. The compound 2,2-bis-[4-(2,3-dicarboxyphenoxy)phenyl]propane dianhydride.

2. The compound 2,2-bis-[4-(3,4-dicarboxyphenoxy)phenyl]propane dianhydride.

* * * * *